United States Patent [19]

Stein et al.

[11] 4,129,561

[45] Dec. 12, 1978

[54] ANTI-ULCER METHANO-DIBENZAZOCINES DERIVATIVES

[75] Inventors: Reinhardt P. Stein, Audubon; Daniel J. Delecki, Royersford, both of Pa.

[73] Assignee: American Home Products Corporation, New York, N.Y.

[21] Appl. No.: 817,392

[22] Filed: Jul. 20, 1977

[51] Int. Cl.² .................... C07D 225/04; A61K 31/55
[52] U.S. Cl. ............................. 260/239 BB; 424/274; 260/239 D
[58] Field of Search ..................... 260/239 BB, 239 D

[56] References Cited

U.S. PATENT DOCUMENTS

| | | | |
|---|---|---|---|
| B 536,935 | 1/1976 | Houlihan et al. | 260/239 D |
| 3,781,270 | 12/1973 | Houlihan et al. | 260/239 BB |
| 3,976,634 | 8/1976 | Nadelson | 260/239 BB |
| 3,985,729 | 10/1976 | Houlihan et al. | 260/239 BB |

*Primary Examiner*—Nicholas S. Rizzo
*Assistant Examiner*—D. B Springer

[57] ABSTRACT

5,6,7,12-Tetrahydro-5,12-methanodibenz[c,f]azocines substituted in the 6-position by a di(lower)alkylaminoacetyl or a di(lower)alkylaminoethyl group inhibit stress-induced ulcers. Also described are intermediates and processes for preparing the anti-ulcer compounds.

4 Claims, No Drawings

ANTI-ULCER METHANO-DIBENZAZOCINES DERIVATIVES

The invention sought to be patented comprises compounds of the formula:

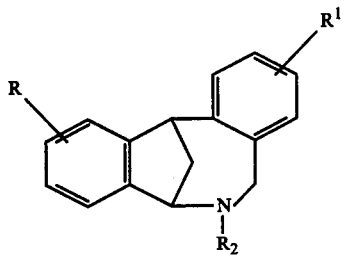

wherein:
R and $R^1$, independently, are hydrogen, (lower)alkyl, (lower)alkoxy, cyclo(lower)alkyl, halo, or phenyl; and $R^2$ is di(lower)alkylaminoacetyl or di(lower)alkylaminoethyl; or an non-toxic acid addition salt thereof.

The compounds of Formula I wherein R and $R^1$ are each hydrogen are preferred.

The compounds of Formula I, wherein R, $R^1$, and $R^2$ have the above-defined meanings, inhibit stress-induced ulcers, as evidenced by standard pharmacological testing in rats.

Also contemplated by this invention are the compounds of the formula:

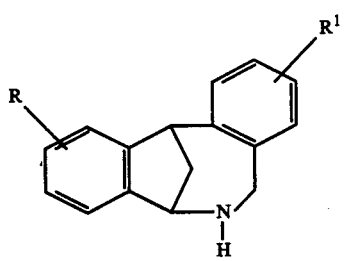

wherein:
R and $R^1$ have the meanings as defined above, or a non-toxic acid addition salt thereof.

The compounds of Formula II are useful as intermediates for the preparation of the anti-ulcer compounds of Formula I. The compound 5,6,7,12-tetrahydro-5,12-methanodibenz[c-f]azocine is preferred.

The compounds of Formula I, wherein $R^2$ is a di(-lower)alkylaminoacetyl group, are prepared in two steps by: (a) reacting a compound of Formula II with chloroacetyl chloride in the presence of pyridine to prepare the N-chloroacetyl derivative and (b) reacting the chloroacetyl derivative with an appropriate di(lower)alkyl amine. The compounds of Formula I, where $R^2$ is a dialkylaminoethyl group are prepared by reducing a compound of Formula I, wherein $R^2$ is a di(lower-)alkylaminoacetyl group, with sodium bis(2-methoxyethoxy)aluminum hydride.

The intermediate compounds of Formula II are prepared by cyclizing a compound of the formula:

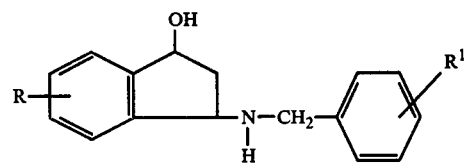

wherein:
R and $R^1$ have the meanings above defined.

The cyclization is accomplished by treating a compound of Formula III with a strong acid. A preferred acid for this purpose is concentrated sulfuric acid, but other carbonium-ionforming reagents (such as 48% hydrobromic and, phosphorus pentoxide in methane sulfonic acid, polyphosphoric acid, or boron trifluoride-ether) may be employed.

The starting materials of Formula III may be prepared by various methods. A preferred method comprises:

(a) reacting a substituted indan-1,3-dione of the formula:

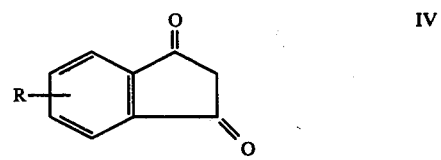

wherein:
R is hydrogen, (lower)alkyl, (lower)alkoxy, cyclo(-lower)alkyl, halo or phenyl with a substituted benzylamine of the formula:

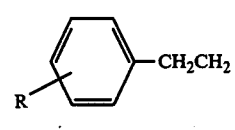

wherein:
$R^1$ is hydrogen, (lower)alkyl, (lower)alkoxy, cyclo(-lower)-alkyl, halo, or phenyl; to afford a mono-imine derivative of Formula VI:

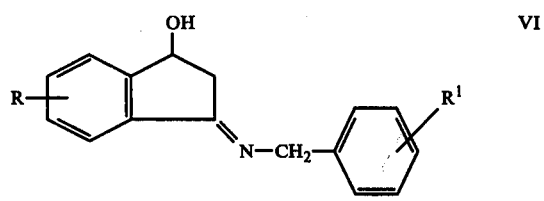

wherein:
R and $R^1$ have the meanings as above defined; and (b) reacting the mono-imine derivative obtained from step (a) with a hydride-donor reducing agent.

In step (a), the reaction is carried out in an inert organic solvent, such as benzene, at a temperature of about 25° C. to about 80° C. A temperature of about 80° C. is preferred.

In step (b), the mono-imine function is reduced to an amine function by reaction with a hydride donor reducing agent. Reagents capable of reducing an imine to an amine are well-known in the art. Examples are the borohydrides (such as sodium borohydride) or the aluminum hydrides (such as lithium aluminum hydride).

The reaction is carried out in an appropriate solvent (for example, methanol, ethanol, or tetrahydrofuran) preferably at room temperature.

An alternative method for preparing the compounds of Formula V is illustrated in Example 2. Although Example 2 describes the preparation of 3-benzylamino-1-indanol from benzylamine and 3-bromo-1-indanone, other 3-benzylamino-1-indanols of Formula V can be prepared by employing a substituted 3-bromo-1-indanone or a substituted benzylamine in which the phenyl groups thereof contain an appropriate substituent (R and $R^1$).

The 3-bromo-1-indanones are prepared from indonones by reaction with N-bromosuccinicimide in the presence of benzoyl peroxide as a free radical catalyst.

The products of the reactions described herein may be isolated and purified by conventional methods. If desired, a compound of Formula I or II may be isolated as an acid addition salt formed by reating the free base with an appropriate nontoxic organic or inorganic acid.

It will be appreciated by those skilled in the art that the compounds of Formula I and the compound 5,6,7,12-tetrahydro5,12-methanodibenz[c,f]azocine contain asymetric carbon atoms and, therefore, said compounds may exist as optically active enantiomorphs. Hence, the compounds may be in the form of the pure enantiomorph or mixtures thereof, such as the the racemates. The compounds may be obtained in the form of a pure enantiomorph either by resolving a desired racemic product or by resolving a racemic starting material or intermediate at any convenient stage of the synthesis. Methods of carrying out the resolution are well known in the art of chemistry. For example, the desired racemate may be treated with an optically active carboxylic acid and the optically active addition salt may be separated by standard techniques.

As employed herein, the term "halo" means a chlorine, bromine, iodine, or fluorine atom. The term "lower" when applied to an alkyl, alkoxy, or dialkylamine function denotes a chain length of from one to six carbon atoms. Methyl, ethyl, and propyl are preferred. The term "cyclo(lower)alkyl" means a cyclopropyl, cyclobutyl, cyclopentyl, or cyclohexyl group.

The following examples are illustrative of the methods for making and using the compounds and processes of the invention.

EXAMPLE 1 dl-3-Benzylamino-1-indanol

Stir indan-1,3-dione (7.31 g.), benzene (200 ml.) and benzylamine (5.90 g.) and reflux into a water separator for 6 hours. Cool, filter, and wash the dark solid with ether. Boil the solid with methylene chloride, filter and remove the solvent by boiling and replace with ether. Filter to get 4.51 g. of dark solid. Stir 4.30 g. of this solid with methanol (150 ml.) and add sodium borohydride (12.0 g.) portionwise with stirring over 4 hours. Let the reaction stand at room temperature then evaporate the solvent in vacuo and digest the residue with water and ether. Extract the mixture with ether and wash, dry and evaporate the solvent in vacuo. Recrystallize the residue from cyclohexane-ether to obtain 1.996 g. of the pure free base of the title compound, m.p. 121°–125°.

Treat the crystalline free base in ethyl acetate-isopropanol with excess isopropanolic-hydrogen chloride to obtain 1.638 g. of the title product as the hydrochloride salt, m.p. 227°–229°.

EXAMPLE 2 dl-3-Benzylamino-1-indanol (Alternative procedure)

Cool a solution of benzylamine (3.22 g.) in dry ether (25 ml.) to below 0° C. With stirring under nitrogen add a cooled (below 0° C.) solution of 3-bromo-1-indanone (3.17 g.) in ether (25 ml.) dropwise over 1.5 hours. Store the reaction under nitrogen at −10° C. for one day. Quickly filter the cold solution and add it cold to a stirring solution of one molar borane in tetrahydrofuran (60 ml.) below 0° C. and under nitrogen. Stir the solution for 18 hours at room temperature. Carefully add a solution of water (3.24 ml.) in tetrahydrofuran (20 ml.) dropwise, followed by 8.0 ml. of 5M isopropanolic —HCl, and continue stirring overnight. Store the reaction at −10° C. overnight, then filter the precipitate through filter-aid. Extract the dry solid mixture with methanol-methylene chloride, filter and evaporate the solvents in vacuo. Triturate the resulting solid with cold ethyl acetate, filter and dry to obtain 2.36 g. of the title product as the hydrochloride salt, m.p. 233–235°. $\lambda_{max}^{KBr}$ 3.0 μ (OH).

Obtain a sample of the free base of the title product by dissolving a sample of the HCl salt above (1.50 g.) in methanol and treating with solid sodium hydroxide (218 mg.) until complete neutralization. Filter and evaporate in vacuo to obtain the title product as the free base, 0.59 g., m.p. 125°–127°.

EXAMPLE 3 dl-5,6,7,12-Tetrahydro-5,12-methanodibenz[c,f]azocine

Add dl-3-benzylamino-1-indanol, hydrochloride (6.086 g.) portionwise to ice-cooled concentrated sulfuric acid (22 ml.) with stirring under nitrogen. After complete addition stir at room temperature a further 2 hours then pour the reaction onto ice. Treat the resulting clear solution with a cold solution of sodium hydroxide (44 g.) in water (440 ml.). Extract the mixture with ether then wash, dry and evaporate the ether in vacuo. Treat the residue in ether-methylene chloride with decolorizing charcoal, filter and evaporate in vacuo. Triturate with hexane to obtain the pure free base of the title product, m.p. 115°–117°.

Analysis for: $C_{16}H_{15}N$ Calculated: C, 86.84; H, 6.83; N, 6.33 Found: C, 86.76; H, 6.71; N, 6.26

Treat the free base with excess isopropanolic-hydrogen chloride in methylene chloride. Evaporate the solvents and pump to obtain 5.184 g. of the title product as the hydrochloride salt, as a white glass.

EXAMPLE 4 dl-6-(Dimethylaminoacetyl)-5,6,7,12-tetrahydro-5,12-methanodibenz[c,f]azocine

Dissolve dl-5,6,7,12-methanodibenz[c,f]azocine (4.21 g.) in benzene (25 ml.), cool with an icebath then add pyridine (1.8 ml.). To the cooled solution add a solution of chloroacetyl chloride (2.24 g.) in benzene (15 ml.) dropwise with stirring over 0.5 hours keeping the temperature below 15° C. Stir cold a further 0.25 hours then at room temperature for 1.5 hours. Add water (12 ml.), stir for 1 hour then separate the benzene layer, wash, dry and evaporate the solvent in vacuo to get 5.58 g. of crude solid. Dissolve this material in 100 ml. of a 30% solution of dimethylamine in methanol and let the reaction stand at room temperature for 4 days. Warm the reaction on the steam-bath for 1 hour, cool and evaporate the mixture in vacuo. Digest the residue by warming with a solution of 7 ml. of 50% NaOH and 14 ml. of water, cool then extract with ether. Wash, dry and evaporate the ether in vacuo to obtain 5.46 g. of the free base of the title product as an oil.

Treat (2.0 g.) in ethyl acetate with excess isopropanolic-hydrogen chloride to obtain 1.98 g. of crude title product as the hydrochloride salt, m.p. 256.5° C. (dec.). Recrystallize from ethyl acetate, m.p. 253.5° (dec).

Analysis for: $C_{20}H_{22}N_2O \cdot HCl$ Calculated: C, 70.06; H, 6.76; N, 8.17; Cl, 10.34 Found: C, 70.12; H, 6.86; N, 8.05; Cl, 10.32

EXAMPLE 5 dl-7,12-Dihydro-N,N-dimethyl-5,12-methanodibenz[c,f]azocine-6(5H)-ethanamine

Add a 1M benzene solution of sodium bis(2-methoxyethoxy)aluminum hydroxide (Red-Al®)(5.3 ml.) dropwise with stirring at room temperature to a solution of dl-6-(dimethylaminoacetyl)-5,6,7,12-tetrahydro-5,12-methanodibenz[c,f]azocine (2.8 g. of the free base) in benzene (27 ml.) over 0.5 hours. Reflux for 2 hours, cool, stir at room temperature then quench by careful addition of saturated aqueous ammonium chloride solution (1.85 ml.) dropwise with stirring. Filter and evaporate the filtrate in vacuo. Dissolve the residue in methylene chloride, wash with water, brine then dry and evaporate the solvent in vacuo to obtain 2.79 g. of the free base of the title product as a viscous oil. Treat the free base with two equivalents of fumaric acid in acetone to obtain the title product as the difumarate salt, m.p. 169°–171.5° C.

Analysis for: $C_{20}H_{24}N_2 \cdot 2C_4H_4O_4$ Calculated: C, 64.11; H, 6.15; N, 5.34 Found: C, 63.81; H, 6.43; N, 4.99

EXAMPLE 6

The anti-ulcer activity of the compounds of Formula I is ellicited and demonstrated by the following test procedure:

Male rats weighing between 120–180 gm. are deprived of food for 18 hours with water ad lib. The rats are divided into groups of ten and dosed by the oral route with test compound or vehicle control, 1.0% methylcellulose, in a volume of 5 ml/kg. Immediately after dosing the animals are inserted into aluminum restraining tubes measuring 1⅝ inches in diameter by 8 inches and placed in the cold (4 ± 1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa are counted by visual observation and recorded; however, since these numbers are so variable, only the incidence of ulcer (i.e., the number of rats with ulcers) are used for evaluation.

The activity of the compounds is assessed by determining a percent inhibition which is calculated as follows:

$$\frac{\% \text{ rats with ulcers in control} - \% \text{ rats with ulcers in treatment} \times 100}{\% \text{ rats with ulcer in control}} = \% \text{ inhibition}$$

Compounds with a greater than 50% inhibition are significantly different from the control group using a corrected Chi square analysis.

When tested as above-described, the compounds dl-6-(dimethylaminoacetyl)-5,6,7,12-tetrahydro-5,12-methanodibenz[c,f]azocine (Example 4) and dl-7,12-dihydro-N,N-dimethyl-5,12-methanodibenz[c,f]azocine-6(5H)-ethanamine (Example 5) representative of the compounds of Formula I, gave 80% inhibition at a dose of 50 mg/kg.

What is claimed is:

1. A compound of the formula:

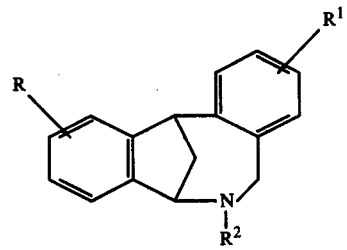

wherein:
R and $R^1$, independently, are hydrogen, (lower)alkyl, (lower)alkoxy, cyclo(lower)alkyl, halo, or phenyl; and
$R^2$ is di(lower)alkylaminoacetyl or di(lower)alkylaminoethyl; or a non-toxic acid addition salt thereof.

2. A compound as defined in claim 1 wherein R and $R^1$ are each hydrogen, or a non-toxic acid addition salt thereof.

3. The compound as defined in claim 2 which is 6-(dimethylaminoacetyl)-5,6,7,12-tetrahydro-5,12-methanodibenz[c,f]azocine.

4. The compound as defined in claim 2 which is 7,12-dihydro-N,N-dimethyl-5,12-methanodibenz[c,f]azocine-6(5H)-ethanamine.

* * * * *